(12) United States Patent
Olek

(10) Patent No.: US 6,977,146 B1
(45) Date of Patent: Dec. 20, 2005

(54) METHOD OF IDENTIFYING CYTOSINE METHYLATION PATTERNS IN GENOMIC DNA SAMPLES

(75) Inventor: Alexander Olek, Berlin (DE)

(73) Assignee: Epigenomics AG, Berlin (DE)

( * ) Notice: Subject to any disclaimer, the term of this patent is extended or adjusted under 35 U.S.C. 154(b) by 0 days.

(21) Appl. No.: 09/890,377

(22) PCT Filed: Jan. 27, 2000

(86) PCT No.: PCT/DE00/00288

§ 371 (c)(1),
(2), (4) Date: Jul. 27, 2001

(87) PCT Pub. No.: WO00/44934

PCT Pub. Date: Aug. 3, 2000

(30) Foreign Application Priority Data

Jan. 29, 1999 (DE) .............................. 199 05 082

(51) Int. Cl.$^7$ .......................... C12Q 1/68; C07H 21/02
(52) U.S. Cl. ........................ 435/6; 435/91.1; 435/91.2; 536/24.3; 536/23.1
(58) Field of Search .................... 435/6, 91.1, 91.2; 536/25.3, 25.4, 24.3; 935/77, 78, 6; 436/518

(56) References Cited

U.S. PATENT DOCUMENTS 5,691,141 A * 11/1997 Koster ............................ 435/6
5,786,146 A     7/1998 Herman et al.
6,265,171 B1 *  7/2001 Herman et al. ................. 435/6

OTHER PUBLICATIONS

Katouzian-Safadi et al., "Identification of the DNA-interacting sites of proteins: Micro sequencing of the peptides cross-linked to 5-bromouracil substituted DNA", Biochimie, (1994), vol. 76 (2), pp. 129-132.*

Herman et al., "Methylation-specific PCR: A novel PCR assay for methylation status of CpG islands," Proc. Natl. Acad. Sci. USA, 93:9821-6 (Sep. 1996).

Frommer et al., "A genomic sequencing protocol that yields a positive display of 5-methylcytosine residues in individual DNA strands," Proc. Natl. Acad. Sci. USA, 89:1827-31.

* cited by examiner

Primary Examiner—Jeffrey Fredman
(74) Attorney, Agent, or Firm—Kriegsman & Kriegsman

(57) ABSTRACT

The invention concerns a method for the identification of cytosine methylation patterns in genomic DNA samples, wherein
  a) a genomic DNA sample is chemically treated such that cytosine and 5-methylcytosine react differently and a different base pairing behavior of the two products results in the duplex;
  b) parts of the thus-treated DNA sample are enzymatically amplified;
  c) the amplified parts of the thus-treated DNA sample bind to a surface;
  d) a set of probes of different nucleobase sequences, each of which contains the dinucleotide sequence 5'-CpG-3' at least once, is hybridized to the immobilized DNA sample;
  e) the non-hybridized probes are separated;
  f) the hybridized probes are analyzed in a mass spectrometer, wherein the position of the probes on the sample holder permits a classification of the hybridizing DNA sample;
  g) Assignment of the peak pattern obtained from the mass spectra to the methylation pattern and comparison of the new data with a database.

23 Claims, No Drawings

METHOD OF IDENTIFYING CYTOSINE METHYLATION PATTERNS IN GENOMIC DNA SAMPLES

The invention concerns a method for the identification of cytosine methylation patterns in genomic DNA samples.

The genetic information which is obtained by complete sequencing of genomic DNA as the base sequence only incompletely describes the genome of a cell. 5-Methylcytosine nucleobases, which are formed by reversible methylation of DNA in the cell, are an epigenetic information carrier and serve, for example, for the regulation of promoters. The methylation state of a genome represents the present status of gene expression, similar to an mRNA expression pattern.

5-Methylcytosine is the most frequent covalently modified base in the DNA of eukaryotic cells. For example, it plays a role in the regulation of transcription, genomic imprinting and in tumorigenesis. The identification of 5-methylcytosine as a component of genetic information is thus of considerable interest. 5-Methylcytosine positions, however, cannot be identified by sequencing, since 5-methylcytosine has the same base pairing behavior as cytosine. In addition, in a PCR amplification, the epigenetic information that is carried by 5-methylcytosine is completely lost.

Several methods are known that attempt to solve these problems. For the most part, a chemical reaction or enzymatic treatment of the genomic DNA is conducted, following which cytosine bases can be distinguished from methylcytosine bases. A current method is the reaction of genomic DNA with bisulfite, which leads to a conversion of cytosine bases to uracil in two steps after alkaline hydrolysis (Shapiro, R., Cohen, B., Servis, R. Nature 227, 1047 (1970). 5-Methylcytosine remains unchanged under these conditions. The conversion of C to U leads to a modification of the base sequence, from which the original 5-methylcytosines can now be determined by sequencing (only these still supply a band in the C lane).

A review of other known possibilities for detecting 5-methylcytosine can be derived, for example, from the following review article: Rein, T., DePamphilis, M. L., Zorbas, H., Nucleic Acids Res. 26, 2255 (1998).

With a few exceptions (e.g., Zeschnigk, M. et al., Eur. J. Hum. Gen. 5, 94–98; Kubota T. et al., Nat. Genet. 16, 16–17), the bisulfate technique has been used previously only in research. Short, specific pieces of a known gene are always amplified, however, after a bisulfite treatment and either completely sequenced (Olek, A. and Walter, J., Nat. Genet. 17, 275–276) or individual cytosine positions are detected by a "primer-extension reaction" (Gonzalgo, M. L. and Jones. P. A., Nucl. Acids Res. 25, 2529–2531) or by enzyme cleavage (Xiong, Z. and Laird, P. W., Nucl., Acids Res. 25, 2532–2534). All of these references derive from the year 1997. The concept of using complex methylation patterns for correlation with phenotypic data of complex genetic disorders is only mentioned in DE-195 43065 A1. For example, the actual detection is not conducted herein by analysis of the hybridization of nucleic acid samples in the mass spectrometer.

It is not always necessary to actually determine the entire sequence of a gene or gene segment, as is the goal in the case of sequencing. This is particularly the case if a few 5-methylcytosine positions within a long base sequence are to be scanned for a multiple number of different samples. Here sequencing supplies redundant information to a great extent and is also very expensive. This is also the case if the sequence is already known and methylation positions exclusively are to be found. It is also conceivable that in several cases, only the differences in the methylation pattern between various genomic DNA samples are of interest in general and that the determination of a multiple number of the same methylated positions can be dispensed with. For the questions introduced here, up until now, there has existed no method which supplies the desired results in a cost-favorable manner without sequencing each individual sample.

Sequence information also needs to be determined less often, since the genome project, whose goal is the complete sequence of various organisms, is rapidly progressing. In fact, at the present time, approximately 5% of the human genome has been sequenced completely, but now, since other genome projects are concluding and sequencing resources are made available in this way, another 5% is added every year. The complete sequencing of the human genome is expected by the year 2006.

Matrix-assisted laser desorption/ionization mass spectrometry (MALDI) is a new, very powerful development for the analysis of biomolecules (Karas, M. and Hillenkamp, F. 1988. Laser desorption ionization of proteins with molecular masses exceeding 10,000 Daltons. Anal. Chem. 60: 2299–2301). An analyte molecule is embedded in a matrix absorbing in the UV. The matrix is evaporated in vacuum by a short laser pulse and the analyte is transported unfragmented into the gas phase. An applied voltage accelerates the ions in a field-free flight tube. Ions are accelerated to varying degree on the basis of their different masses. Smaller ions reach the detector sooner than larger ions. The time-of-flight is converted to the mass of the ions.

Technical innovations of the hardware have significantly improved the method. The "delayed extraction" (DE) method is worthy of mention. For DE, the acceleration voltage for the laser pulse is turned on with a delay, and in this way an improved resolution of signals is achieved, since the number of collisions is reduced.

MALDI is excellently suitable for the analysis of peptides and proteins. For nucleic acids, the sensitivity is approximately 100 times poorer than for peptides and decreases overproportionally with increasing fragment size. The reason for this lies in the fact that only a single proton must be captured for the ionization of peptides and proteins. For nucleic acids, which have a backbone with a multiple negative charge, the ionization process via the matrix is essentially inefficient. For MALDI, the choice of matrix plays an extremely important role. For the desorption of peptides, several very powerful matrices have been found, which result in a very fine crystallization. In fact, several suitable matrices have now been found for DNA, but the difference in sensitivity was not reduced thereby. Phosphorothionate nucleic acids, in which the usual phosphates of the backbone are substituted by thiophosphates, can be converted to a charge-neutral DNA by simple alkylation chemistry.

The coupling of a "charge tag" to this modified DNA results in an increase of sensitivity to the same range as is found for peptides. By these modifications, it is now also possible to utilize matrices that are similar to those that are used for the desorption of peptides. Another advantage of charge tagging is the increased stability of analysis when impurities are present, which greatly complicate the detection of unmodified substrates. PNAs and methylphosphonate oligonucleotides have been investigated with MALDI and can thus be analyzed.

Presently this technology can distinguish molecules with a mass difference of 1 Da in the mass region from 1,000 to 4,000 Da. Due to the natural distribution of isotopes, most biomolecules, however, are approximated within a range of 5 Da. Technically, this mass-spectrometric method is thus very suitable for the analysis of biomolecules. Reasonably, the products to be analyzed, which are to be distinguished, must lie at least 5 Da apart from one another. Therefore, 600 molecules could be distinguished in this mass region.

An array with many thousand target DNAs can be immobilized on a solid-phase support and then all of these target DNAs can be investigated jointly for the presence of a sequence by means of a probe (nucleic acid with complementary sequence).

A correspondence of the target DNA with the probe is achieved by a hybridization of the two parts with one another. Probes can be any nucleic acid sequences of any length. Different methods exist for the selection of optimal libraries of probe sequences, which minimally overlap. Probe sequences can be prepared for the purpose of finding specific target DNA sequences. Oligofingerprinting is an approach in which this technology is utilized. A library of target DNAs is scanned with short nucleic acid probes. For the most part, the probes in this case are only 8–12 bases long. Each time a probe is hybridized once onto a target DNA library immobilized on a nylon membrane. The probe is radioactively labeled and the hybridization is evaluated on the basis of localizing the radioactivity. For scanning an immobilized DNA array, fluorescently labeled probes have also been used.

U.S. Pat. No. 5,605,798 describes the scanning of target nucleic acids that have been immobilized by hybridizing with nucleic acid probes and mass spectrometry. However, an identification of methylation patterns is not specifically conducted, nor are modified nucleic acids (e.g. PNAs, charge tags) utilized, nor is a genome amplification conducted.

Any molecules can be used as probes, which can interact in a sequence-specific manner with a target DNA. Oligodeoxyribonucleotides are used most often currently. However, any modification of nucleic acids, e.g., peptide nucleic acids (PNA), phosphorothioate oligonucleotides or methylphosphonate oligonucleotides can be used. The specificity of a probe is most essential. Phosphorothioate oligonucleotides are not entirely suitable, since their structure is disrupted by sulfur atoms and the hybridization property is also disrupted thereby. A reason for this could be that the phosphorothioate oligonucleotides are normally not synthesized as pure diastereomers. In the case of methylphosphonate oligonucleotides, a similar problem exists, but these oligonucleotides are synthesized and propagated as pure diastereomers. An essential difference in this modification is the uncharged backbone, which leads to a reduced dependence of hybridization on buffer salts and overall leads to higher affinity due to fewer repulsions. Peptide nucleic acids also have an uncharged backbone, which simultaneously deviates chemically very greatly from the familiar sugar-phosphate structure of the backbone in nucleic acids. The backbone of a PNA has an amide sequence instead of the sugar-phosphate backbone of conventional DNA. PNA hybridizes very well with DNA of complementary sequence. The melting point of a PNA/DNA hybrid is higher than that of the corresponding DNA/DNA hybrid and again the dependence of hybridization on buffer salts is relatively small.

Combinatory syntheses, i.e., the preparation of substance libraries proceeding from a mixture of precursors, are conducted both in the solid phase as well as in the liquid phase. Combinatory solid-phase synthesis can be completed in a very short time, since in this case, the separation of byproducts is very simple. Only the target compounds that are bound to the support are retained in one washing step and are isolated at the end of the synthesis by the targeted cleavage of a linker. This technique permits in a simple way the simultaneous synthesis of a multiple number of different compounds on a solid phase and thus obtaining chemically "pure" substance libraries.

Compound classes, which are also synthesized on a solid phase in non-combinatory, conventional syntheses, are thus particularly accessible to combinatory chemistry and are consequently also very widely used. This particularly concerns peptide, nucleic acid and PNA libraries.

Peptides are synthesized by binding the first N-protected amino acid (e.g., Boc) to the support, subsequent de-protection and reaction of the second amino acid with the $NH_2$ group that has been released from the first. Unreacted amino functions are withdrawn in an additional "capping" step of a further reaction in the next synthesis cycle. The protective group of the amino function of the second amino acid is removed and the next building block can be coupled. A mixture of amino acids is used in one or more steps for the synthesis of peptide libraries. The synthesis of PNA and PNA libraries is conducted rationally.

Nucleic acid libraries are obtained for the most part by solid-phase synthesis with mixtures of different phosphoramidite nucleosides. This can be carried out on commercially obtainable DNA synthesizers without modifications in the synthesis protocols.

Various studies for combinatory synthesis of PNA libraries have been published. These studies concern the structure of combinatory sequences, i.e., the synthesis of PNAs in which individual, specific bases in the sequence are replaced by degenerated bases and in this way random sequence variance is achieved.

The use of mass-spectrometric methods for the analysis of combinatory libraries has been described many times.

Different methods exist for immobilizing DNA. The best known method is the fixed binding of DNA, which is functionalized with biotin, to a streptavidin-coated surface. The binding strength of this system corresponds to a covalent chemical bond without being one. In order to be able to bind a target DNA covalently to a chemically prepared surface, a corresponding functionality of the target DNA is required. DNA itself does not possess a functionalization that is suitable. There are different variants in a target DNA for introducing a suitable functionalization: two easy-to-manipulate functionalizations are primary, aliphatic amines and thiols. Such amines are quantitatively converted with N-hydroxy succinimide esters, and thiols react quantitatively with alkyl iodides under suitable conditions. However, it is difficult to introduce such a functionalization into a DNA. The simplest variant is introduction by means of a primer of a PCR. Targeted variants utilize 5'-modified primers ($NH_2$ and SH) and a bifunctional linker.

An essential component for immobilization onto a surface is the nature of this surface. Systems described up until now are primarily comprised of silicon or metal (magnetic beads). Another method for binding a target DNA is based on using a short recognition sequence (e.g., 20 bases) in the target DNA for hybridizing to a surface-immobilized oligonucleotide.

Enzymatic variants have also been described for introducing chemically activated positions into a target DNA. Here, a 5'-$NH_2$ functionalization is enzymatically introduced in a target DNA.

The object of the present invention is to create a method, which overcomes the disadvantages of the state of the art and can indicate cytosine methylations effectively and in a highly parallel manner, in an array of immobilized genomic DNA samples.

The subject of the present invention is thus a method for finding epigenetic information carriers in the form of 5-methylcytosine bases in genomic DNA, which uses a multiple number of probes simultaneously for mass-spectrometric investigation of an array of target nucleic acids.

The object is solved according to the invention by making available a method for the identification of cytosine methylation patterns in genomic DNA samples, by:
a) chemically treating a genomic DNA sample in such a way that cytosine and 5-methylcytosine react differently and obtaining a different base pairing behavior of the two products in the duplex;
b) enzymatically amplifying portions of the thus-treated DNA sample;
c) binding the amplified portions of the thus-treated DNA sample to a surface;
d) hybridizing a set of probes of different nucleobase sequences, each of which contains the dinucleotide sequence 5'-CpG-3' at least once, to the immobilized DNA sample;
e) separating the non-hybridized probes;
f) analyzing the hybridized probes in a mass spectrometer, wherein the position of the probes on the sample holder permits a classification of the hybridizing DNA sample;
g) assignment of the peak pattern obtained from the mass spectra to the methylation pattern and comparison of the new data with a database.

It is preferred according to the invention that one or more amplified genomic DNA fragments is (are) immobilized in c) by hybridization with complementary oligonucleotide or PNA sequences, which are bound covalently to the surface.

It is further preferred according to the invention that after the hybridization, a cross-linking of the genomic DNA fragments is produced with the oligonucleotide or PNA sequences bound to the surface. It is particularly preferred here that covalent chemical bonds are formed for the cross-linking. It is also preferred according to the invention that electrostatic interactions are formed for the cross-linking.

It is of further advantage that the oligonucleotide or PNA sequences which are bound to the surface contain 5-bromouracil structural units.

It is preferred according to the invention that the immobilized complementary oligonucleotide sequences contain modified bases, ribose or backbone units.

The method according to the invention is further characterized in that the genomic DNA probe is propagated in b) in the form of several amplified fragments, so that at least 0.01% of the entire genome is amplified.

It is also preferred according to the invention that the mixture of amplified DNA fragments is bound onto a surface on which a multiple number of different points is arranged, each of which can bind different portions of the amplified DNA sample.

According to the invention, it is further preferred that a set of probes be used in d), which contains the dinucleotide sequence 5'-CpG-3' only once per probe and otherwise, each of the probes contain either no cytosine or no guanine bases.

It is also preferred according to the invention that a bisulfite or pyrosulfite or disulfite solution or a mixture of the indicated solutions is used in step a), together with other reagents, for the specific or sufficiently selective conversion of cytosine to uracil.

It is also advantageous that the surface used for the immobilization of amplified sample DNA is also the sample holder for a mass spectrometer. It is preferred that the surface used for the immobilization of amplified sample DNA is introduced as a whole, prior to f), onto a sample holder for a mass spectrometer. It is also preferred here that the hybridized probes are stripped from the immobilized, amplified DNA samples before, after, or by contact with a matrix.

It is further preferred according to the invention that the probes are nucleic acids, which bear one or several mass tags. It is also advantageous according to the invention that one or more mass tags are also charge tags. Or that the probes also have a charge tag.

It is preferred according to the invention that the probes are modified nucleic acid molecules. It is particularly preferred that the modified nucleic acid molecules are PNAs, alkylated phosphorothioate nucleic acids or alkyl phosphonate nucleic acids.

It is preferred according to the invention that the probes are produced by combinatory synthesis. It is particularly preferred according to the invention that the various base structural units are labeled in such a way that each of the probes synthesized from them can be distinguished by their mass in the mass spectrometer.

It is of further advantage according to the invention that the probes are produced as sublibraries and are provided with various mass and/or charge tags.

It is most preferred according to the invention that matrix-assisted laser desorption/ionization mass spectrometry (MALDI) is used in f).

Another subject of the present invention is a kit for conducting the method according to the invention, which contains the following: a sample holder for a mass spectrometer, which is modified such that randomly selectable parts of a genome can be immobilized onto this holder, and/or probe libraries with which the DNA immobilized to the sample holder is analyzed by the mass spectrometer, and/or other chemicals, solvents and/or adjuvants, as well as, optionally, instructions for use.

The method according to the invention serves for the identification of 5-methylcytosine positions in genomic DNA which can have various origins. The genomic DNA is first treated chemically in such a way that there is a difference in the reaction of cytosine bases and 5-methylcytosine bases. Possible reagents here are, e.g., disulfite (also designated bisulfite), hydrazine and permanganate. In a preferred variant of the method, the genomic DNA is treated with disulfite in the presence of hydroquinone or hydroquinone derivatives, whereby the cytosine bases are selectively converted into uracil after subsequent alkali hydrolysis. 5-Methylcytosine remains unchanged under these conditions. After a purification process, which serves for the separation of excess disulfite, specific segments of the pretreated genomic DNA are amplified in a polymerase reaction. In a preferred variant of the method, the polymerase chain reaction is used here. In a particularly preferred variant of the method, the polymerase chain reaction is conducted in such a way that at least 0.01% of the total genome is amplified in the form of several fragments.

The amplified, pretreated DNA sample can now be immobilized onto a surface in several variants of the method. In a preferred variant of the method, immobilization to the surface is conducted in such a way that the surface has been modified beforehand with oligonucleotides or short PNA (peptide nucleic acid) sequences and thus a hybridization of complementary sequences in the DNA sample results. Basically, the immobilized oligonucleotides can be modified at bases, at (deoxy)ribose and/or at the backbone, in contrast to conventional DNA. Now if different oligonucleotide or PNA sequences are bound to this surface in the form of an array or are synthesized on it, each of these different sequences can bind different portions of the amplified DNA fragments. In a particularly preferred variant of the method, a cross-linking of the two strands is conducted subsequent to the hybridization. This can result from the formation of a covalent chemical bond or a stable electrostatic interaction. In another preferred variant, a photochemical cross-linking is conducted by means of bromouracil structural units.

It is also possible to separately amplify fragments of the pretreated genomic DNA and to immobilize the products individually at different sites on the surface. In a preferred variant of the method, this is performed in such a way that one of the PCR primers bears a function suitable for immobilization, which can enter into a bond with a functionality introduced onto the surface.

The surface, to which the amplified DNA fragments are bound, will either be transferred onto the sample holder of a MALDI mass spectrometer or will be this sample holder itself. The construction and software of the mass spectrometer thus assure that the investigated point on the sample holder can be assigned each time to the sample originally bound there.

A set of probes is now hybridized to the immobilized, amplified DNA fragments, whereby these probes each contain the sequence 5'-CpG-3' at least once and otherwise do not contain either cytosine or guanine bases. The probes can be oligonucleotides, modified oligonucleotides or PNAs (peptide nucleic acids). In a preferred variant of the method, this set of probes is produced as a combinatory library in a combinatory synthesis approach. In another preferred variant of the method, the probes can be clearly distinguished by their mass, so that it is possible to conclude the sequence from the mass. For this purpose, the probes can be provided with mass tags, which prevent the various probes from being of equal mass. The probes can be provided with charge tags in order to achieve a better presentation in the mass spectrometer and to increase the the analysis in the presence of salts and detergents. The mass tags may also be charge tags. The probes may also be prepared as combinatory sublibraries, which in turn bear different mass and/or charge tags. The probes can be PNAs, unmodified nucleic acid molecules or modified nucleic acid molecules such as phosphothioate nucleic acids, alkylated phosphorothioate nucleic acids or alkyl phosphonate nucleic acids, regardless of further modification by mass and charge tags.

The non-hybridized probes are separated in one or more washing steps. The hybridized probes thus remain at their positions.

The surface is fastened to the MALDI sample holder and transferred to the mass spectrometer or transferred directly if the method has been conducted on the MALDI sample holder itself. The array of samples is now investigated by mass spectrometer on hybridized probes. The hybridized probes are dehybridized for this purpose by contact with the MALDI matrix and embedded in it in a preferred variant of the method; however no cross-contamination of adjacent points results due to the rate at which the matrix is introduced. The hybridized probes provide a peak pattern at each point, by means of which the sequence can be derived, at which a hybridization has occurred. Due to the pretreatment (preferably with bisulfite), different sequences result for DNA fragments methylated differently at the cytosine. Therefore, each of the characteristic methylation patterns of the investigated DNA sample is the peak pattern produced by the probe in the mass spectrometer. Then these methylation patterns are compared with those of a database.

What is claimed is:

1. Method for identifying cytosine methylation patterns in genomic DNA samples, said method comprising the steps of:
    a) chemically treating a genomic DNA sample in such a way that cytosine and 5-methylcytosine react differently and a different base pairing behavior of the two products is obtained in the duplex;
    b) enzymatically amplifying portions of the thus-treated DNA sample;
    c) binding the amplified portions of the thus-treated DNA sample to a surface;
    d) contacting a set of probes of different nucleobase sequences, each of which contains the dinucleotide sequence 5'-CpG-3' at least once, to the immobilized DNA samples for hybridization to distinguish methylated and nonmethylated cytosines in said genomic DNA sample;
    e) removing any non-hybridized probes from the immobilized DNA samples;
    f) analyzing the hybridized probes in a mass spectrometer, wherein the position of the hybridized probes on the surface permits a classification of the immobilized DNA sample hybridized thereto;
    g) assigning a peak pattern obtained from the mass spectra to a methylation pattern for the immobilized DNA and comparing the peak pattern with a database to identify cytosine methylation patterns in the genomic DNA sample.

2. Method according to claim 1, further characterized in that one or more amplified genomic DNA fragments are immobilized in c) by hybridization with complementary oligonucleotide or PNA sequences, which are covalently bound to the surface.

3. Method according to claim 2, further characterized in that a cross-linking of the genomic DNA fragments with the oligonucleotide or PNA sequences bound to the surface results after the hybridization.

4. Method according to claim 3, further characterized in that covalent chemical bonds are formed for the cross-linking.

5. Method according to claim 3, further characterized in that electrostatic interactions are formed for the cross-linking.

6. Method according to claim 3, further characterized in that the oligonucleotide or PNA sequences bound to the surface contain 5-bromouracil structural units.

7. Method according to claim 1, further characterized in that the immobilized complementary oligonucleotide sequences contain modified bases, ribose or backbone units.

8. Method according to claim 1, further characterized in that the genomic DNA sample is propagated in b) in the form of several amplified fragments, so that at least 0.01% of the total genome is amplified.

9. Method according to claim 1, further characterized in that the mixture of amplified DNA fragments is bound to a surface, on which a multiple number of different points is arranged, each of which can bind different portions of the amplified DNA sample.

10. Method according to claim 1, further characterized in that a set of probes is used in d), which contains the dinucleotide sequence 5'-CpG-3' only once in each probe and the probes otherwise contain either no cytosine or no guanine bases.

11. Method according to claim 1, further characterized in that a bisulfite or pyrosulfite or disulfite solution or a mixture of the indicated solutions is used together with other reagents for the specific or sufficiently selective conversion of cytosine to uracil.

12. Method according to claim 1, further characterized in that the surface used for the immobilization of amplified sample DNA is also the sample holder for a mass spectrometer.

13. Method according to claim 1, further characterized in that the surface used for the immobilization of amplified sample DNA is introduced as a whole, prior to f), onto a sample holder for a mass spectrometer.

14. Method according to claim 1, further characterized in that the hybridized probes are stripped from the immobilized amplified DNA samples before, after or by contact with a matrix.

15. Method according to claim 1, further characterized in that the probes are nucleic acids, which bear one or more mass tags.

16. Method according to claim 15, further characterized in that one or more mass tags are also charge tags.

17. Method according to claim 15, further characterized in that the probes also bear a charge tag.

18. Method according to claim 1, further characterized in that the probes are modified nucleic acid molecules.

19. Method according to claim 2, further characterized in that nucleic acid molecules are selected from the group consisting of PNAs, alkylated phosphorothioate nucleic acids and alkyl phosphonate nucleic acids.

20. Method according to claim 1, further characterized in that the probes are prepared by combinatory synthesis.

21. Method according to claim 20, further characterized in that different base structural units are labeled in such a way that each of the probes synthesized from them can be distinguished by their mass in the mass spectrometer.

22. Method according to claim 1, further characterized in that the probes are prepared as sublibraries and these are provided with different mass and/or charge tags.

23. Method according to one of the preceding claims, further characterized in that matrix-assisted laser desorption/ionization mass spectrometry (MALDI) is conducted in f).

* * * * *